US012648826B2

(12) United States Patent
Dougherty et al.

(10) Patent No.: US 12,648,826 B2
(45) Date of Patent: Jun. 9, 2026

(54) CRANIAL BURR HOLE INTRODUCER FOR SURGICAL ACCESS

(71) Applicant: Stryker Corporation, Portage, MI (US)

(72) Inventors: Brian C. Dougherty, Terra Haute, IN (US); Joseph L Mark, Indianapolis, IN (US)

(73) Assignee: Stryker Corporation, Portage, MI (US)

( * ) Notice: Subject to any disclaimer, the term of this patent is extended or adjusted under 35 U.S.C. 154(b) by 610 days.

(21) Appl. No.: 17/721,155

(22) Filed: Apr. 14, 2022

(65) Prior Publication Data

US 2023/0329824 A1 Oct. 19, 2023

(51) Int. Cl.
| | |
|---|---|
| *A61B 90/11* | (2016.01) |
| *A61B 17/34* | (2006.01) |
| *A61B 90/10* | (2016.01) |
| *A61B 1/04* | (2006.01) |
| *A61B 1/313* | (2006.01) |
| *A61B 17/00* | (2006.01) |
| *A61B 90/00* | (2016.01) |

(52) U.S. Cl.
CPC .......... *A61B 90/10* (2016.02); *A61B 17/3468* (2013.01); *A61B 1/04* (2013.01); *A61B 1/313* (2013.01); *A61B 2017/00486* (2013.01); *A61B 2017/00951* (2013.01); *A61B 2090/033* (2016.02); *A61B 2090/103* (2016.02)

(58) Field of Classification Search
CPC ............ A61B 17/3468; A61B 17/3494; A61B 2017/3492; A61B 2017/00486; A61B 2017/00951; A61B 1/04; A61B 1/313; A61B 90/10; A61B 2090/033; A61B 2090/103; A61B 90/11; A61B 17/3403; A61B 17/3423; A61B 90/14; A61M 2039/025; A61M 39/0247; A61M 2039/0279
USPC .......................... 600/184; 606/108, 184, 185
See application file for complete search history.

(56) References Cited

U.S. PATENT DOCUMENTS

| | | | | |
|---|---|---|---|---|
| 4,681,103 A * | 7/1987 | Boner ................ | A61B 17/3403 | 606/1 |
| 4,805,615 A * | 2/1989 | Carol ..................... | A61B 90/11 | 403/115 |
| 4,809,694 A * | 3/1989 | Ferrara .............. | A61B 17/3403 | 606/130 |
| 5,217,441 A * | 6/1993 | Shichman .......... | A61B 17/3496 | 604/536 |
| 5,993,471 A * | 11/1999 | Riza .................... | A61B 17/3498 | 606/185 |
| 10,219,799 B2 * | 3/2019 | Pattison ............. | A61B 17/0057 | |
| 2002/0052610 A1 * | 5/2002 | Skakoon ................ | A61B 34/20 | 606/129 |
| 2011/0054518 A1 * | 3/2011 | Carbunaru ......... | A61B 17/3415 | 606/213 |

* cited by examiner

*Primary Examiner* — Kathleen S Holwerda
(74) *Attorney, Agent, or Firm* — Howard & Howard Attorneys PLLC

(57) ABSTRACT

A medical device for accessing soft tissue of the brain may include a delivery sleeve assembly including a sheath configured to receive a surgical access device and mate with a socket arrangement of a cranial burr hole device arranged on a patient, and a depth stop arranged on the sheath of the delivery sleeve assembly configured to be selectively adjusted along the sheath to an incremental depth marker associated with the location of a surgical site.

14 Claims, 7 Drawing Sheets

CRANIAL BURR HOLE INTRODUCER FOR SURGICAL ACCESS

TECHNICAL FIELD

The present disclosure relates generally to a surgical access system for use with delicate and critical tissues, as well as methods of accessing and performing surgery using same.

BACKGROUND

Diagnosis and treatment of conditions affecting the brain are among the most difficult and complex problems that face the medical profession. The brain is a complex and delicate soft multi-component tissue structure that controls bodily functions through a complex neural network connected to the rest of the body through the spinal cord. The brain and spinal cord are contained within and protected by significant bony structures, e.g., the skull and the spine. Given the difficulty of accessing the brain through the hard bony protective skull and the delicate network and complex interactions that form the neural communication network contained within the brain that define the human body's ability to carry on its functions of speech, sight, hearing, functional mobility, reasoning, emotions, respiration and other metabolic functions, the diagnosis and treatment of brain anomalies such as intracranial vascular bleeds presents unique challenges not encountered elsewhere in the body. Under the best of hospital conditions and state of the art equipment, the management of intracranial bleeds are a health crisis for the patient and challenging for the multi-disciplinary healthcare team tasked with saving the patient's life. However, when a vascular crisis occurs on the battle-field or in a mass population trauma event, the management of a vascular cranial trauma becomes even more challenging and often times intervention must be performed to achieve stabilization of the patient by a field medic, not a neurosur-geon or field doctor. There is a need for a device which can be implemented in field related trauma event which allows for a field medic to stabilize the patient so that transport to a qualified medical facility can be achieved safely for the patient.

SUMMARY

A medical device for accessing soft tissue of the brain may include a delivery sleeve assembly including a sheath configured to receive a surgical access device and mate with a socket arrangement of a cranial burr hole device arranged on a patient, and a depth stop arranged on the sheath of the delivery sleeve assembly configured to be selectively adjusted along the sheath to an incremental depth marker associated with the location of a surgical site.

A socket assembly for mating with a cranial burr hole device and receiving a surgical access device for accessing soft tissue of the brain may include a socket top having a socket opening configured to receive a surgical access device, and a socket bottom configured to be received by a burr hole device opening in the cranial burr hole device and to mate with the socket top.

BRIEF DESCRIPTION OF THE DRAWINGS

Exemplary embodiments of the present disclosure will now be described in greater detail with reference to the attached figures, in which.

DETAILED DESCRIPTION

Figure 1:
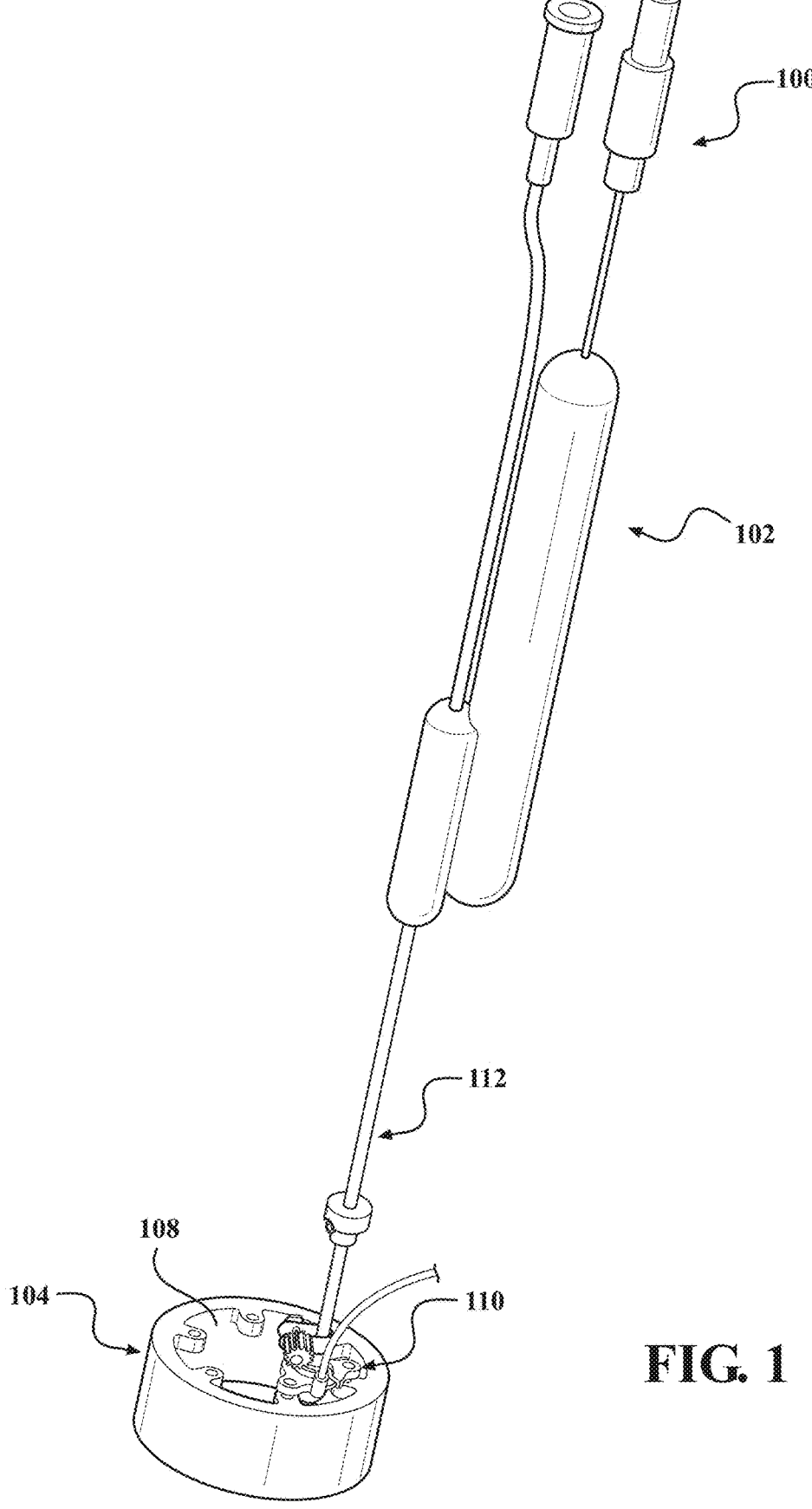
FIG. 1 illustrates a perspective view of a surgical access system.

Referring now to the discussion that follows and also to the drawings, illustrative approaches to the disclosed assem-blies and methods are shown in detail. Although the draw-ings represent some possible approaches, the drawings are not necessarily to scale and certain features may be exag-gerated, removed, or partially sectioned to better illustrate and explain the present disclosure. Further, the descriptions set forth herein are not intended to be exhaustive or other-wise limit or restrict the claims to the precise forms and configurations shown in the drawings and disclosed in the following detailed description.

Surgical access systems may provide medical profession-als with an enhanced ability to minimize trauma to the patient, while providing efficient improved minimally inva-sive surgical techniques, such as, for example, during intrac-ranial surgical techniques. Such devices may also be used for application of targeted and effective treatment regimens.

Specifically, head trauma in combat or military situations may often occur remote from medical facilities or remote locations where high level of care may not be immediately available. In these situations, an individual may suffer a brain injury, such as a hematoma, brain bruise, brain clot, etc., without the ability to reach a hospital or other facility for hours.

Described herein is an interventional field-care device for critically addressing an epidural or subdural hematoma and/or active bleed quickly within the field. Other ancillary devices may be used in conjunction with the inventive interventional device described herein, Examples of other ancillary devices are a device to allow for non-invasive detection of the sub-cranial hematoma's location, including information as to the depth and volume/size of the formed hematoma. Further, ancillary devices may be configured to create access to the sub-cranial clot by creating a mini-craniotomy, such as a burr hole craniotomy thus allowing the device described herein minimally invasive access for the subsequent removal of the hematoma and the management of active bleeding at the point of injury. This could decrease morbidity and increase survivability and quality of life after head trauma suffered on the field.

The device may include an introducer to be used with a minimally invasive surgical burr hole craniotomy mount. The introducer may be inserted into a burr hole mount arranged on the patient's head. A socket is fitted onto the burr hole mount and configured to mate the introducer with the burr hole mount. The introducer may include incremental depth marks that correspond to the top of the socket, allowing the operator to know the degree of advancement of the surgical access device. The surgical access device may then access the surgical site via the introducer to resect the necessary tissue to reduce the intracranial pressure (ICP). The device may be packaged as part of a kit to be compact, lightweight and mobile, and be considered "backpack ready" for field use.

FIG. 1 illustrates an example surgical access system 100. The surgical access system 100 may include a surgical access device 102 configured to resect tissue. The surgical access device 102 may be in one example, the NICO MYRIAD® manufactured and distributed by Nico Corporation of Indianapolis, Ind. The surgical access system 100 may include a cranial burr hole device 104 (also referred to herein as burr hole mount 104). The cranial burr hole device 104 may be configured to be affixed to an injured person's cranium or scalp. The cranial burr hole mount 104 may allow for a scanning of non-invasive scanning of the cranium to locate potential injured tissue, such as a sub-cranial hematoma. The cranial burr hole device 104 may also provide information to the operator as to the thickness of the hematoma. However, in another case, a device separate from the cranial burr hole device 104 may determine this information.

The burr hole device 104 may allow access for drilling into the cranium and may include an opening to receive a drill. The burr hole device may include a membrane 108 to protect the open area under the burr hole device 104 from debris, or other particles to decrease the chance of infection during a procedure in the field.

A socket arrangement 110 may be arranged at an opening in the membrane 108 (not labeled in FIG. 1), and may be configured to receive a delivery sleeve assembly 112 extending from the surgical access device 102. The delivery sleeve assembly 112 may facilitate access to the area of interest and may include a delivery sleeve, resection device, etc. The delivery sleeve assembly 112 may also receive and provide irrigation fluid and or could include the use of a hemostatic agent to the area of interest.

Figure 2:
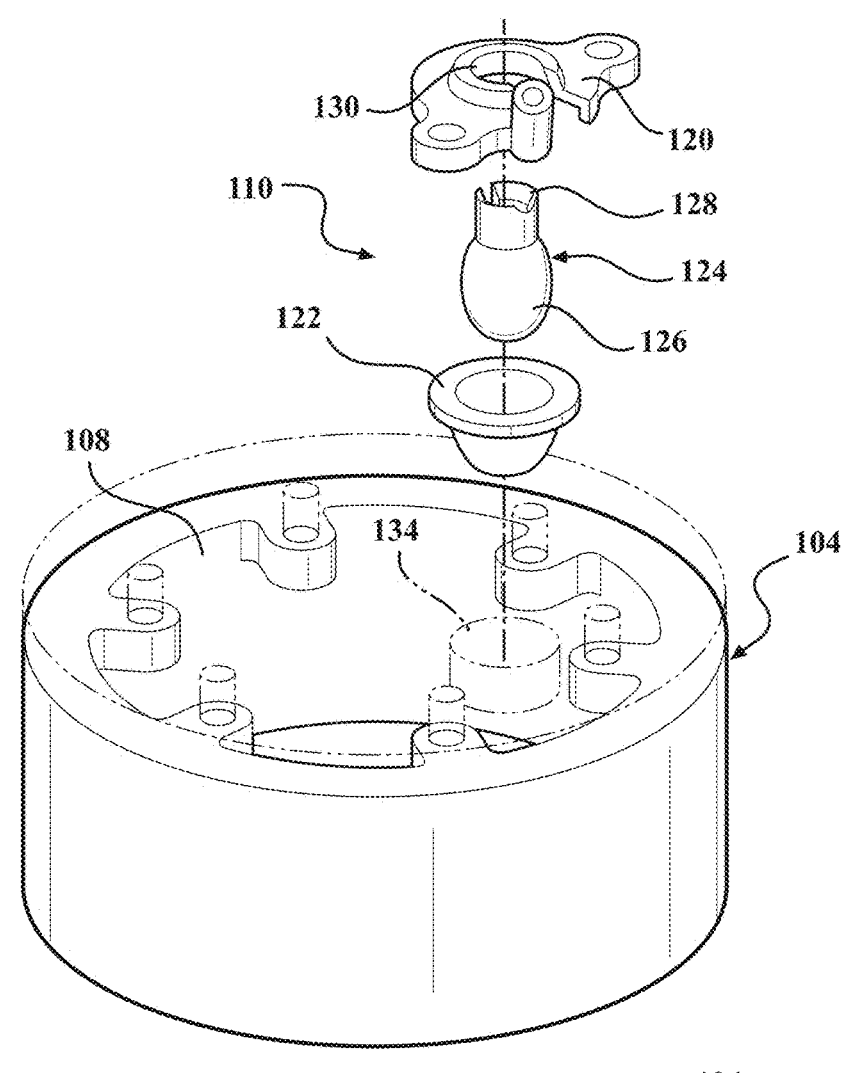
FIG. 2 illustrates an exploded view of a socket arrange-ment and a cranial burr hole mount of the surgical access system of FIG. 1.
Figure 3:
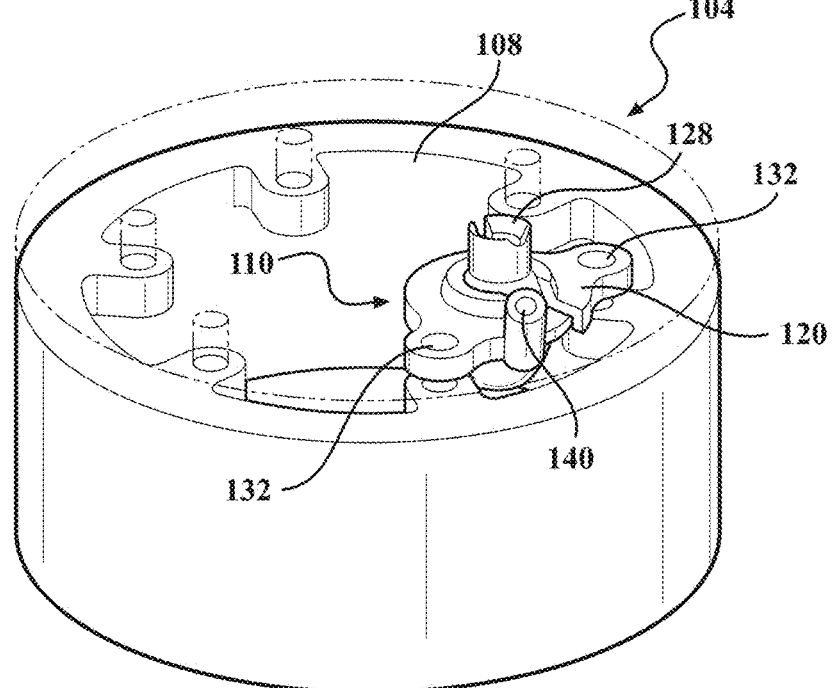
FIG. 3 illustrates a perspective view of the socket arrange-ment and cranial burr hole device of FIG. 2.

FIG. 2 illustrates an exploded view of the socket arrangement 110 and the cranial burr hole device 104 of the surgical access system 100 of FIG. 1. FIG. 3 illustrates a perspective view of the socket arrangement 110 and cranial burr hole device 104 of FIG. 2. The socket arrangement 110 may be installed on the cranial burr hole device 104 so that the cranial burr hole device 104 is ready to use, attach to the cranium and receive the delivery sleeve assembly 112 of the surgical access device 102.

Referring to FIGS. 2 and 3, the socket arrangement 110 may include a socket top 120 and a socket bottom 122. A ball 124 may be arranged between the socket top 120 and the socket bottom 122 and may include a ball portion 126 and a lip 128. The socket bottom 122 may have a conical shape and may be configured to receive the ball portion 126 of the ball 124. The socket top 120 may define a socket opening 130 configured to receive the lip 128.

In the assembled state, as best illustrated in FIG. 3, the lip 128 may protrude from the socket opening 130 of the socket top 120. The socket top 120 may be fixed to the cranial burr hole device 104 by a connecting piece (not shown), such as a threaded engagement, friction fit, a screw, a snap fit, an interlock mechanism, adhesive or various other removable attachment mechanisms which would produce a tight seal or barrier to preclude the ingress of particulates and or biological microbes, received by the area around fastener openings 132 on each side or around the socket top 120. The fastener openings 132 may align with openings on the cranial burr hole device 104 to receive the connecting piece, such as a screw. The lip 128 may be configured to receive a distal end of the delivery sleeve assembly 112, as discussed herein. The ball 124 may be formed of silicone or rubber-like materials to allow a seal to be created between the delivery sleeve assembly 112 and the socket arrangement 110. The ball 124 may form a snap-fit ball-and-socket configuration. Further examples of the interface and interlock of the cranial burr hole device 104 with the socket arrangement 110 are illustrated and described in more detail with respect to FIG. 10.

The membrane 108 may define a membrane opening 134 configured to receive the socket bottom 122. The conical shape of the socket bottom 122 may fit within the membrane opening 134 and create a seal against the membrane opening 134. The socket bottom 122 may be similarly formed from silicon or rubber-like materials. The ball 124 and the socket bottom 122 may each define an opening at the bottom sides thereof in order to allow access to the surgical site or area of interest. The socket top 120 may be formed of a plastic or metal material and form a rigid structure between the cranial burr hole device 104 and the ball 124 and socket bottom 122.

The socket top 120 may also define a camera opening 140 configured to receive a flexible camera, fiberoptic cable, and/or other device, such as a light source. This is described in more detail herein with respect to FIG. 9 and may allow for direct viewing of the surgical site. In one example, the opening may be approximately 1.2 mm in diameter. The camera opening 140 may allow access through the socket top 120 to the surgical site. In some examples, the camera opening 140 may be arranged elsewhere within or on the socket top 120, as well as within the ball.

Figure 4:
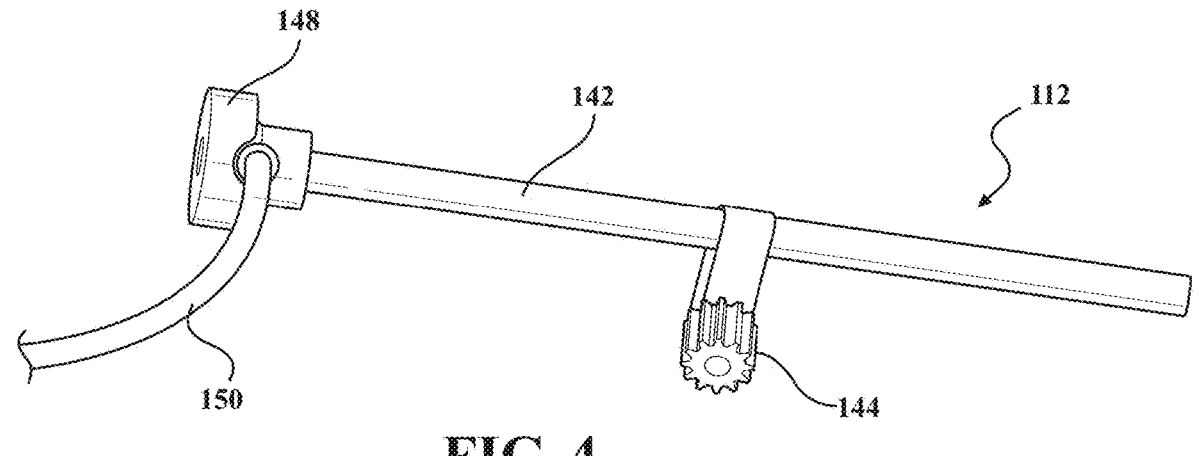
FIG. 4 illustrates a perspective view of a delivery sleeve assembly of the surgical access system of FIG. 1.
Figure 5:
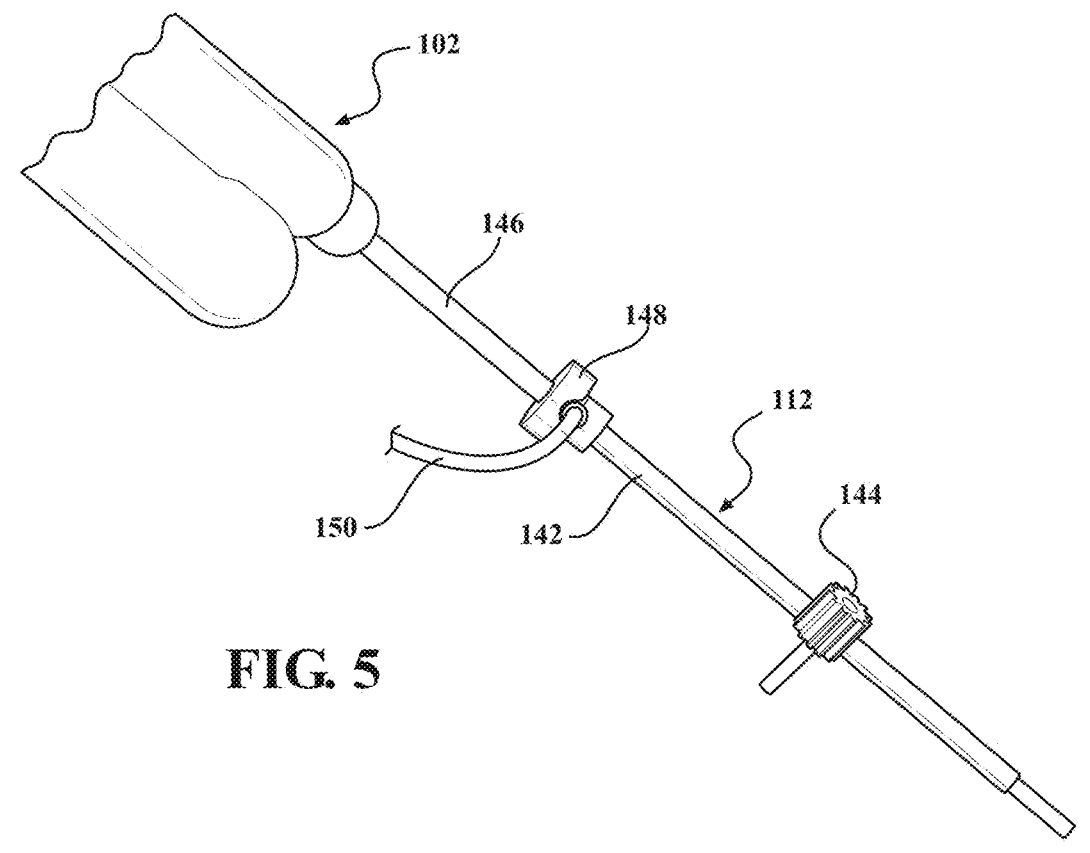
FIG. 5 illustrates a perspective view of the delivery sleeve assembly arranged on the surgical access device of FIG. 1.

FIG. 4 illustrates a perspective view of the delivery sleeve assembly 112 of the surgical access system 100 of FIG. 1. FIG. 5 illustrates a perspective view of the delivery sleeve assembly 112 arranged on the surgical access device 102 of FIG. 1.

Referring to FIGS. 4 and 5, the delivery sleeve assembly 112 is configured to work with and on the surgical access device 102 in order to achieve access to the surgical site. The delivery sleeve assembly 112 may include a sheath 142 to provide an access port to the surgical site. The sheath 142 or delivery sleeve may be configured to receive stylets, resection tools, etc. The delivery sleeve assembly 112 may include a depth stop 144 arranged on the sheath 142. The depth stop 144 may be movable along the sheath 142 and may be selectively set at a fixed position along the sheath 142. The depth stop 144 may abut the socket assembly 110 once the sheath 142 is advanced into the surgical site. A separate non-invasive imaging device may be used to determine the location and indicate the depth of the hematoma. This information may be presented to the user and allow the depth stop 144 to be set accordingly, with the height of the burr hole mount 104 and socket arrangement 110 taken into account. In another example, the cranial burr hole device 104 may be capable of performing the imaging.

The depth stop 144 may include a rotatable dial configured to apply pressure and clamp the depth stop 144 to the sheath 142 in the fixed position. Rotation of the dial in an opposite direction may loosen the depth stop 144 with respect to the sheath 142 to allow for movement along the sheath 142.

To maintain the delivery sleeve assembly 112 in position on the surgical access device 102, the delivery sleeve assembly 112 may include an adaptor arrangement 148. The adaptor arrangement 148 may be configured to lock the delivery sleeve assembly 112 to a cannula 146 of the surgical access device 102. This is discussed in more detail with respect to FIGS. 6 and 7.

The delivery sleeve assembly 112 may further include an irrigation port 150 configured to be received by the adaptor arrangement 148. This may allow for fluid to be delivered through sheath 142.

Figure 6:
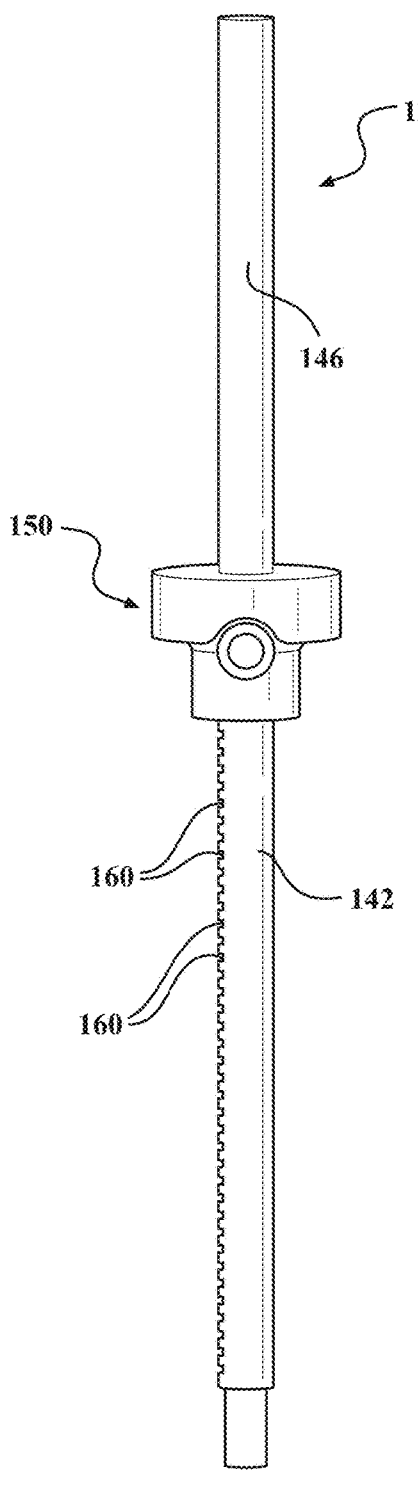
FIG. 6 illustrates a front view of the delivery sleeve assembly of FIG. 4.

FIG. 6 illustrates a front view of the delivery sleeve assembly 112 of FIG. 4. The sheath 142 may include incremental depth marks 160 that correspond to the top of the socket arrangement 110 so that the user is aware of the depth as the surgical access device 102 is advanced. The adaptor arrangement 148 may be twisted along the sheath 142 to the desired depth. In one example, the adaptor arrangement 148 may form a helical or screw-like arrangement with the sheath 142.

Figure 7:
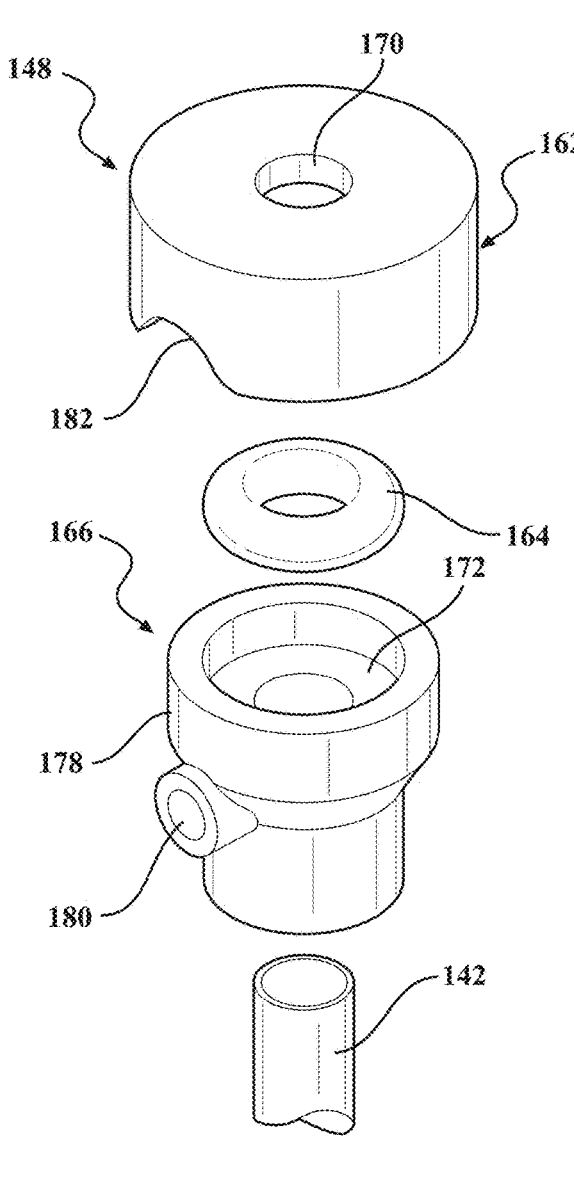
FIG. 7 illustrates an exploded view of the adaptor arrange-ment for the delivery sheath assembly of FIG. 4.

FIG. 7 illustrates an exploded view of the adaptor arrangement 148 for the delivery sleeve assembly 112 of FIG. 4. The adaptor arrangement 148 may include a sheath adaptor cap 162, an o-ring 164, and a sheath adaptor 166. The sheath adaptor 166 may form an adaptor lip 178 configured to form a recess 172 configured to receive the o-ring 164 such that the o-ring 164 may be seated therein. The sheath adaptor cap 162 may have a central opening 170 and form a hallow interior configured to receive the adaptor lip 178 and seal the o-ring 164 within the recess 172 of the sheath adaptor 166. The sheath adaptor 166 may have a hollow channel aligned with the cap central opening 170 configured to receive a resection tool (not shown) of the surgical access device 102.

A port socket 180 may be arranged on a side of the sheath adaptor 166 and be configured to receive the irrigation port 150 (as shown in FIGS. 5 and 6). The sheath adapter cap 162 may define a notch 182 to accommodate the port socket 180 and irrigation port 150 in the assembled stated.

Figure 8:
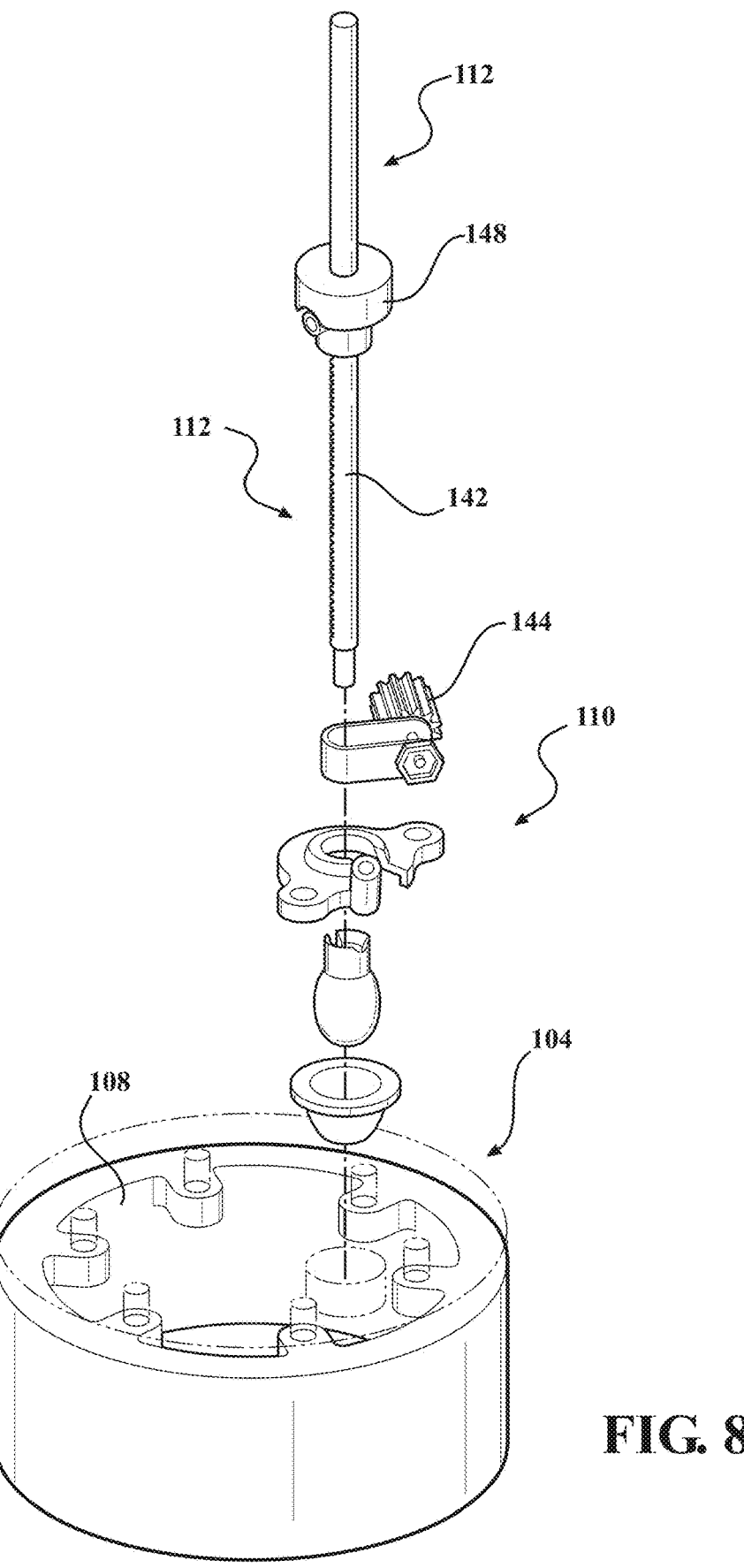
FIG. 8 illustrates an exploded view of the introducer assembly, socket arrangement, and cranial burr hole.

FIG. 8 illustrates an exploded view of the delivery sleeve assembly 112, socket arrangement 110, and cranial burr hole device 104. The depth stop 144 is also illustrated. In operation, the depth stop 144 may prevent advancement of the sheath 142 by abutting the adaptor arrangement 148.

Figure 9:
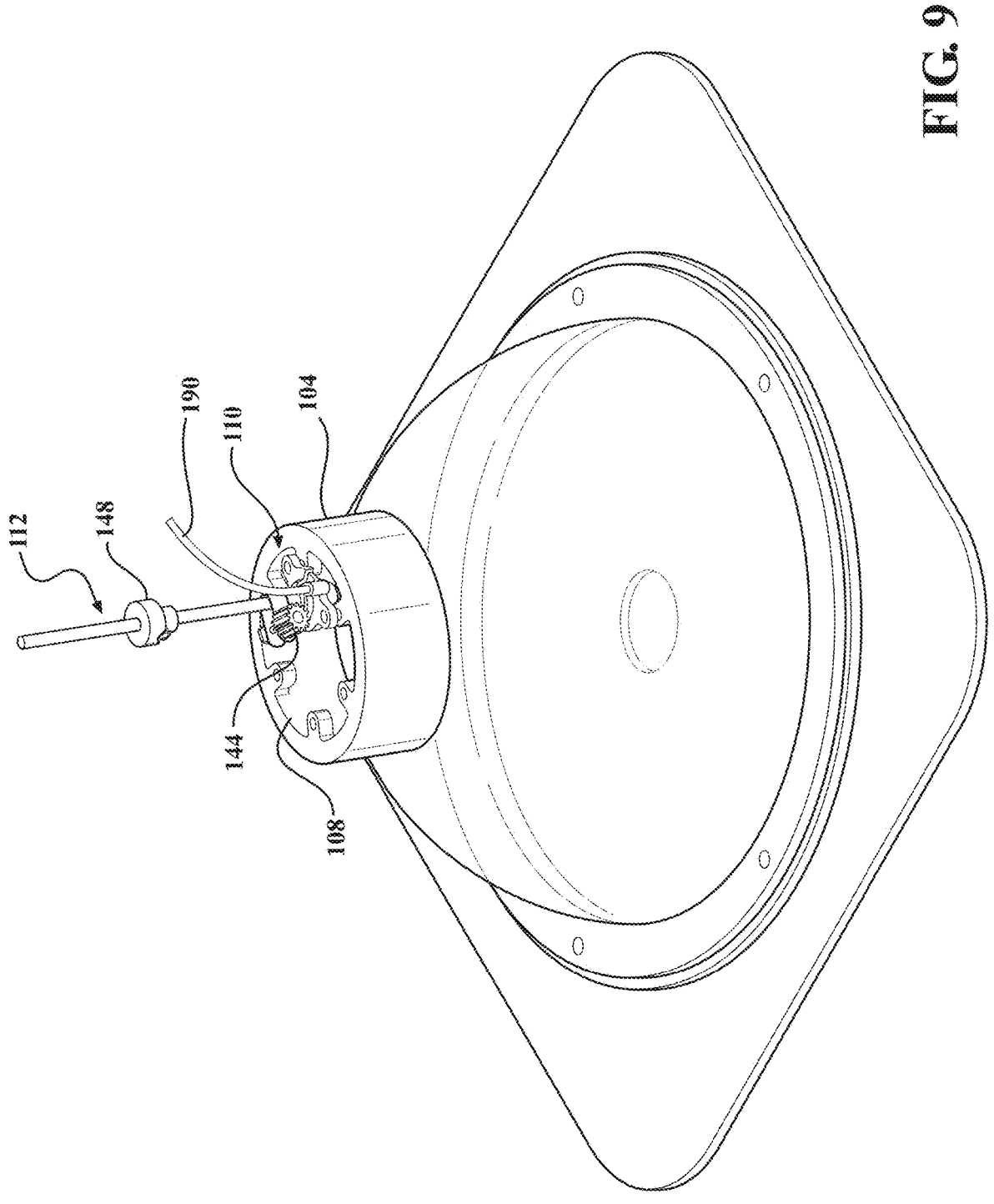
FIG. 9 illustrates a perspective view of a portion of the surgical access assembly including a camera.

FIG. 9 illustrates a perspective view of a portion of the surgical access assembly including a camera 190. As explained above, the camera 190 may be received by the camera opening 140 of the socket arrangement 110, as best illustrated in FIG. 3. The camera 190 may allow for direct viewing of the surgical site. The camera 190 may provide the correct light to the surgical site, such as white light, or infrared light (for night vision). Other devices or instruments may also be inserted into the camera opening 140.

In operation, once an injury is detected, the area of the injury on the scalp may be shaved in order to remove the patient's hair from the surgical area and appropriate surgical prep is applied. The cranial burr hole device 104 may then be fixed to the area, for example, by adhesive. The cranium may then be drilled to provide access to the underlying soft tissue. The cranial burr hole device 104 may determine the size, depth, location, etc., of the clot or hematoma. In another example, a device separate and distinct from the burr hole mount 104 may determine the size, depth, location, etc., of the abnormality. Once this is determined the cranial burr hole device 104 may provide this information to the operator of the device. This may be done via a user interface (not shown) either on the cranial burr hole device 104 or an adjacent connected device (either wired or wirelessly connected), such as a mobile device.

The depth stop 144 may then be set to the appropriate position on the sheath 142 of the delivery sleeve assembly 112. The surgical access device 102 may then be advanced to the surgical site by inserting the sheath 142 of the delivery sleeve assembly 112 into the membrane opening 134 in the membrane 108 of the cranial burr hole device 104. Once the sheath 142 is inserted, the resection device of the surgical access device 102 may access and treat the surgical site. The resection device may be inserted until the depth stop 144 abuts the socket arrangement 110, preventing over-insertion of the surgical access device 102.

If necessary, irrigation may be provided to the surgical site via the irrigation port 150 of the delivery sleeve assembly 112. Once the surgical site has been treated, the surgical access device 102 may be removed. In one example, the delivery sleeve assembly 112 may be removed with the surgical access device 102, or in another example, may be removed separately from the surgical access device 102. Once the sheath 142 has been removed, the cranial burr hole device 104 may also be removed and the dura, skull and scalp closed.

Several options for integrating with the cranial burr device 104 may be possible and the surgical access device 102 may access the surgical site in several ways through the socket arrangement 110. In one example, the cranial burr device 104 may include a membrane on the underside of the mount. The socket arrangement 110 may be seated and create a sealed fit with the membrane. In this example, the resecting device of the surgical access device 102 may extend through the cylinder of the cranial burr device 104 to reach and extend through the socket arrangement 110.

In another example, the cranial burr device 104 may include additional tools and features arranged on the membrane. In one example, a drill or drill accessory may be preinstalled on the membrane. Once the cranium is drilled, the cranial burr device 104 may include a top rotational cylinder that rotates relative to a bottom stationary cylinder. Rotation of the top cylinder may move the drill out of the way, and allow a new item, such as the socket arrangement 110, to be arranged over the surgical site. Once the socket arrangement 110 is arranged over the surgical site, the surgical access device 102 may be received by the socket arrangement 110 to access the surgical site.

In another example, the drill or other parts may be removed to allow the socket arrangement 110 to be accessible for the surgical access device 102. In this example, it may not be necessary for the cranial burr device 104 to rotate or move. Regardless, the socket and the delivery sleeve assembly 112 of the surgical access device 102 are used to provide in field treatment. While the cranial burr device 104 is discussed and illustrated herein, these are merely example renderings. In some cases, the cranial burr device 104 may not be necessary and the user may access the surgical site directly.

Figure 10:
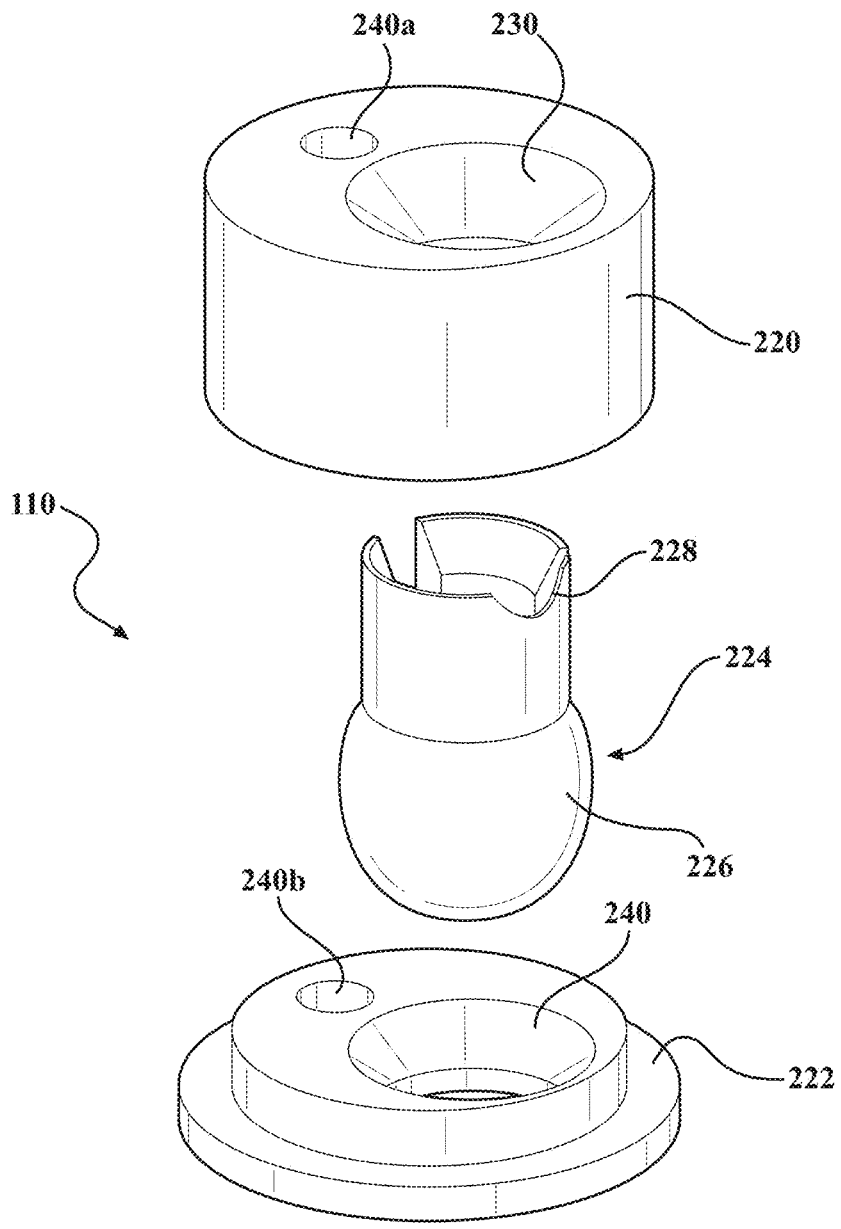
FIG. 10 illustrates an exploded view of another example adaptor arrangement.

FIG. 10 illustrates another example socket arrangement 110 having a socket top 220 and a socket bottom 222. A ball 224 may be arranged between the socket top 220 and the socket bottom 222 and may include a ball portion 226 and a lip portion 228. The socket bottom 222 may have a cylindrical shape and may be configured to receive the ball portion 226 of the ball 224 within a bottom opening 240. The socket top 220 may define a socket opening 230 configured to receive the lip 228 of the ball 224.

In the assembled state, the lip 228 may be seated within the socket opening 230 of the socket top 220. The socket top

220 may receive a raised portion of the socket bottom 222 to mate with the socket bottom 222. The lip 228 may be configured to receive a distal end of the delivery sleeve assembly 112, as discussed herein. The ball 224 may be formed of silicone or rubber-like materials to allow a seal to be created between the delivery sleeve assembly 112 and the socket arrangement 110. As with FIGS. 2 and 3, the ball 224 may form a snap-fit ball-and-socket configuration.

The socket top 220 and socket bottom 222, when mated, may define a camera opening 240 created from a top camera opening 240*a* and a bottom camera opening 240*b*. The channel created by the camera openings 240 may be configured to receive a flexible camera, fiberoptic cable, and/or other device, such as a light source.

The socket example in FIG. 10 may be attached to the cranial burr device 104 in a similar manner as that shown in FIGS. 2-3 where an attachment opening 132 of the socket aligns with an opening of the cranial burr hole device 104 and receives an attachment mechanism such as a screw, etc. Additionally or alternatively, a tenon may extend from the socket bottom 222 and be received by one of the openings in the cranial burr hole device 104. Other such friction-fit, including tapered and straight fittings and openings may be used. The burr device opening (not shown in FIG. 10) may be approximately 10 mm in size. Other forms of attachment may be contemplated. In one example, a rubber bung may be used to twist a locking mechanism to engage a sealing member, or a twist-lock. In another example, a latch or clamp, or a plurality thereof or combination thereof may be used. Other threaded attachments such as screws, set screws, bolts, threaded joint, etc., may be used.

Other forms of attaching the socket arrangement 110 to the cranial burr hole device 104 may include using various adhesives, either alone or in combination with the other methods and mechanisms discussed herein. With many of the mechanisms described herein, an o-ring or gasket may be used between the socket top and the socket bottom, and/or between the socket parts and the cranial burr hole device 104.

As explained, the surgical access system 100 may be provided as part of a kit. The example kits are provided separately as single use devices, in sterilized containers or pouches. The kits may be compact and easily carried through combat.

Further, while the described system is discussed in the contact of combat, other applications and uses may benefit from the described surgical access systems, including but not limited to first responders, storable first aid, use in areas remote from a hospital, disaster locations, etc.

While the above-described system provides the advantage of creating direct access to an area of interest, including an area of interest in the subcortical space, thereby permitting debulking of the area of interest to reduce the Intracranial Pressure to stabilize the patient for safe transport, as well as delivery of a therapy if available of an in-situ (without the encumbrance and limitations encountered with systemic therapy delivery), to mitigate certain intracranial trauma conditions, additional subsequent therapy may be warranted for increased therapeutic benefits.

It will be appreciated that the surgical access system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A medical device for accessing soft tissue of the brain, comprising:

a cranial burr hole device configured to be arranged on a patient;

a socket arrangement including:

a socket top defining a socket top opening, a socket bottom defining a socket bottom opening and configured to be received by a burr hole device opening in the cranial burr hole device, and a ball having a ball portion and a lip extending upward from the ball portion, the ball portion seated within the socket bottom and the lip received by the socket top;

a delivery sleeve assembly including a sheath configured to receive a surgical access device, wherein the socket top opening, the socket bottom opening, and the lip are configured to receive the sheath when the cranial burr hole device is arranged on a patient; and a depth stop arranged on the sheath of the delivery sleeve assembly configured to be selectively adjusted along the sheath to an incremental depth marker associated with the location of a surgical site, wherein the socket top defines at least one camera opening separate from and non-concentric with the socket top opening and the socket bottom defines at least one camera opening separate from and non-concentric with the socket bottom opening, the socket top being configured to mate with the socket bottom such that one of the at least one camera opening of the socket top aligns with one of the at least one camera opening of the socket bottom to define a channel through the socket arrangement that is configured to receive a camera so that the camera may access the surgical site via the socket arrangement.

2. The medical device of claim 1, wherein the delivery sleeve assembly includes an adaptor assembly configured to fix the delivery sleeve assembly to the surgical access device.

3. The medical device of claim 2, wherein the adaptor assembly includes a sheath adaptor defining a channel configured to receive the sheath and an irrigation socket configured to receive an irrigation port.

4. The medical device of claim 3, wherein the adaptor assembly includes an adaptor cap configured to cover at least a portion of the sheath adaptor and receive a resection tool of the surgical access device.

5. The medical device of claim 4, wherein the sheath adaptor is configured to receive an O-ring, and wherein the adaptor cap is configured to seal the O-ring within the sheath adaptor in an assembled state.

6. The medical device of claim 1, wherein the socket bottom forms a conical shape configured to mimic the ball portion of the seated ball.

7. The medical device of claim 1, wherein the ball portion of the ball is configured to be received by at least a portion of the socket bottom opening.

8. The medical device of claim 1, wherein the socket bottom creates a seal with a membrane of the cranial burr hole device.

9. The medical device of claim 1, wherein the socket top defines a fastener opening configured to align with at least one burr hole device attachment opening, each configured to receive a fastener to attach the socket arrangement to the cranial burr hole device.

10. The medical device of claim 1, wherein at least one of the socket top and socket bottom are attached to the cranial burr hole device via an adhesive.

11. The medical device of claim 1, wherein at least one of the socket top and socket bottom are attached to the cranial burr hole device via a friction fit mechanism.

12. The medical device of claim 1, wherein at least one of the socket top and socket bottom are attached to the cranial burr hole device via a screw and threaded opening.

13. The medical device of claim 1, wherein the cranial burr hole device comprises:

a cylinder having opposed first and second open ends and defining a volume extending between the first and second open ends, the first open end configured to affix to a cranium; and a membrane positioned across the second open end and defining the burr hole device opening, wherein the socket arrangement is received in the burr hole device opening of the membrane to create a seal with the membrane and such that the volume defined by the cylinder is positioned between the cranium and the socket arrangement when the first open end is affixed to the cranium.

14. A medical device for accessing soft tissue of the brain, comprising:

a socket arrangement including a socket top defining a socket opening, wherein the socket top defines at least one camera opening separate from and non-concentric with the socket opening, the at least one camera opening configured to receive a camera so that the camera may access a surgical site via the socket arrangement;

a cranial burr hole device configured to be arranged on a patient, the cranial bur hole device including:

a cylinder having opposed first and second open ends and defining a volume extending between the first and second open ends, the first open end configured to affix to a cranium, and a membrane positioned across the second open end and defining an opening, wherein the socket arrangement is received in the opening of the membrane to create a seal with the membrane and such that the volume defined by the cylinder is positioned between the cranium and the socket arrangement when the first open end is affixed to the cranium;

a delivery sleeve assembly including a sheath configured to receive a surgical access device, wherein the socket opening is configured to receive the sheath when the cranial burr hole device is arranged on the patient; and a depth stop arranged on the sheath of the delivery sleeve assembly configured to be selectively adjusted along the sheath to an incremental depth marker associated with the location of the surgical site.

\* \* \* \* \*